(12) United States Patent
Willsie (10) Patent No.: US 10,898,167 B2
(45) Date of Patent: Jan. 26, 2021

(54) PORTABLE ULTRASOUND SYSTEMS WITH FINE-GRAINED POWER MANAGEMENT ASSOCIATED DEVICES, SYSTEMS, AND METHODS

(71) Applicant: FUJIFILM Sonosite, Inc., Bothell, WA (US)

(72) Inventor: Todd Willsie, Seattle, WA (US)

(73) Assignee: FUJIFILM SONOSITE, INC., Bothell, WA (US)

( * ) Notice: Subject to any disclaimer, the term of this patent is extended or adjusted under 35 U.S.C. 154(b) by 386 days.

(21) Appl. No.: 14/339,385

(22) Filed: Jul. 23, 2014

(65) Prior Publication Data

US 2015/0031999 A1    Jan. 29, 2015

Related U.S. Application Data

(60) Provisional application No. 61/858,052, filed on Jul. 24, 2013.

(51) Int. Cl.
*A61B 8/00* (2006.01)
*G01S 7/52* (2006.01)
*A61B 8/14* (2006.01)

(52) U.S. Cl.
CPC .............. *A61B 8/56* (2013.01); *A61B 8/4427* (2013.01); *G01S 7/52096* (2013.01); *A61B 8/145* (2013.01); *G01S 7/52017* (2013.01)

(58) Field of Classification Search
CPC ........... A61B 8/00; A61B 8/56; A61B 8/4427; A61B 8/145; G01S 7/52096; G01S 7/52017; G06F 1/32
See application file for complete search history.

(56) References Cited

U.S. PATENT DOCUMENTS

| | | | | |
|---|---|---|---|---|
| 4,827,911 | A * | 5/1989 | Broadwin | A61B 17/22012 310/17 |
| 6,251,073 | B1 * | 6/2001 | Imran | A61B 8/08 600/443 |
| 6,471,651 | B1 * | 10/2002 | Hwang | A61B 8/00 600/437 |
| 7,399,279 | B2 * | 7/2008 | Abend | A61B 8/06 600/450 |
| 7,996,688 | B2 * | 8/2011 | Little | G01S 7/52096 713/300 |
| 9,775,585 | B2 * | 10/2017 | Miller | G01S 7/52034 |
| 2003/0095013 | A1 * | 5/2003 | Melanson | H02M 3/1584 332/109 |
| 2006/0264747 | A1 * | 11/2006 | Freeman | G01S 7/52025 600/437 |

(Continued)

*Primary Examiner* — Luther Behringer
(74) *Attorney, Agent, or Firm* — Womble Bond Dickinson (US) LLP (57) ABSTRACT

Portable ultrasound systems and associated devices and methods for managing power in such systems are disclosed herein. In one embodiment, a method for conserving power in a portable ultrasound system includes disabling one or more first amplifiers and/or at least one or more first analog to digital converters (ADCs) upon initiation of a first pulse repetition interval (PRI). The method further includes, upon initiation of a second PRI, enabling the one or more first amplifiers and/or the one or more of the first ADCs and disabling one or more second amplifiers of and/or one or more second ADCs.

18 Claims, 11 Drawing Sheets

(56) References Cited

U.S. PATENT DOCUMENTS

| | | | | |
|---|---|---|---|---|
| 2008/0110263 A1* | 5/2008 | Klessel | ............... | G01S 7/52028 |
| | | | | 73/602 |
| 2008/0312534 A1* | 12/2008 | Pitsillides | ............ | A61B 5/0031 |
| | | | | 600/455 |
| 2009/0045994 A1* | 2/2009 | Drummy | .............. | G01N 29/262 |
| | | | | 341/155 |
| 2010/0213882 A1* | 8/2010 | Adachi | ................. | H02N 2/004 |
| | | | | 318/116 |
| 2011/0222419 A1* | 9/2011 | Callaway, Jr. | .... | H04W 52/0261 |
| | | | | 370/252 |
| 2012/0323121 A1* | 12/2012 | Miller | ................. | A61B 8/4488 |
| | | | | 600/443 |
| 2013/0303919 A1* | 11/2013 | Corl | .................... | A61B 8/4494 |
| | | | | 600/467 |

* cited by examiner

PORTABLE ULTRASOUND SYSTEMS WITH FINE-GRAINED POWER MANAGEMENT ASSOCIATED DEVICES, SYSTEMS, AND METHODS

CROSS-REFERENCES TO RELATED APPLICATIONS

This application claims benefit of U.S. Patent Provisional Application Ser. No. 61/858,052, filed on Jul. 24, 2013 and entitled "PORTABLE ULTRASOUND SYSTEMS WITH FINE-GRAINED POWER MANAGEMENT ASSOCIATED DEVICES, SYSTEMS, AND METHODS", which is hereby incorporated herein in its entirety by reference.

TECHNICAL FIELD

The disclosed technology is related to medical imaging systems, and, in particular, some embodiments are related to portable ultrasound devices and power management in such devices.

BACKGROUND

Portable ultrasound imaging devices are used by anesthesiologists, emergency and critical care personnel, and other medical professionals. A portable ultrasound device can include a clamshell-type base unit having a handle for carrying the base unit. The base unit can fold open to a display and a keypad, and a user can connect an ultrasound transducer wand to the base unit to acquire and view ultrasound images on the display.

BRIEF DESCRIPTION OF THE DRAWINGS

FIGS. 5A-7B are signal line diagrams representing the power consumed by amplifiers and/or analog to digital converters during execution of the routine of FIG. 3 over various duty cycles in accordance with selected embodiments of the present technology.

DETAILED DESCRIPTION

Various embodiments of portable ultrasound devices and power management techniques and associated devices, systems, and methods are described below. A person skilled in the relevant art, however, will understand that the technology may have additional embodiments, and that the technology may be practiced without several of the details of the embodiments described below with reference to FIGS. 1-7B.

Ultrasound devices include a variety of electronic components configured, for example, to generate and receive acoustic signals, process and store data, and display images. In a portable ultrasound device, each of the electronic components draws power from the battery based on its individual power requirements. Transducer-related circuitry, in particular, draws a significant amount of power. This circuitry can include, for example, waveform generators, transducer arrays, amplifiers, and analog to digital converters (ADCs). Of these components, the amplifiers and the ADCs draw a large portion of the power. In some instances, an ultrasound device can temporarily disable (e.g., remove power, shut down, etc.) certain components to conserve power when not in an imaging mode. However, many of the components are difficult to disable. In particular, amplifiers and ADCs require a significant amount of time to power-on and power-off. As such, it is not possible to power down these components to conserve power without sacrificing device performance, such as system speed. Embodiments of the present technology, however, address these and other limitations of conventional portable ultrasound devices.

Figure 1:
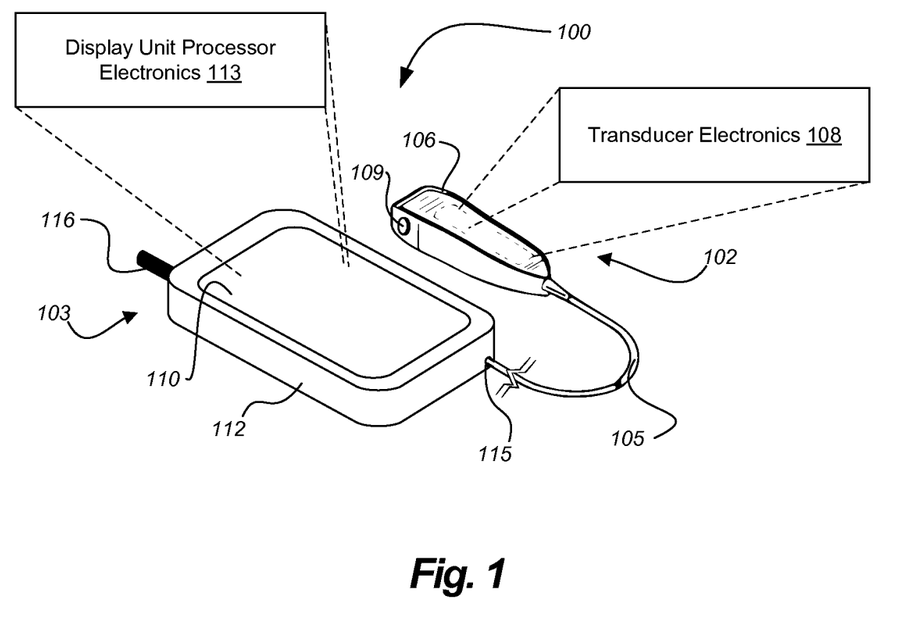
FIG. 1 is a partially schematic, isometric diagram of an ultrasound system configured in accordance with an embodiment of the present technology.

FIG. 1 is a block diagram of a portable ultrasound system 100 configured in accordance with an embodiment of the present technology. The ultrasound system 100 includes a transducer wand 102, a display unit 103, and a signal line 105 (e.g., a permanent or removable signal wire) operably coupling the transducer wand 102 with the display unit 103. The transducer wand 102 includes an enclosure 106, transducer electronics 108 at least partially contained by the enclosure 106, and at least one input device 109 (e.g., a button, trigger, etc.) at the enclosure 106 and operably coupled to the transducer electronics 108. As described in greater detail below, the transducer electronics 108 are configured to generate and receive acoustic signals, transmit and receive data, and/or otherwise process acoustic, digital, and analog signals. In one embodiment, the input device 109 is configured to toggle the ultrasound system 100 between an imaging mode and a scan mode. For example, the input device 109 can provide a user with a convenient way to toggle between modes without having to directly operate the display unit 103. In another embodiment, however, the input device 109 can be omitted. Although not shown for purposes of clarity, the transducer wand 102 can include other features. For example, the enclosure 106 can have a variety of shapes, sizes, and configurations (e.g., ergonomic configurations) depending on the application or other considerations.

The display unit 103 can include a touch-screen display 110, a housing 112, display unit (processor) electronics 113 (shown schematically) at least partially contained by the housing 112, and at least one I/O port 115 (e.g., for communication with the transducer electronics 108 via the signal line 105). The touch-screen display 110 is configured to receive user-input and to present or display information, such as an image, a web-browser, an application interface, etc. In certain embodiments, the housing 112 can include controls (not shown), such as buttons, switches, or knobs in addition to or in lieu of the touch-screen display. The display unit electronics 113 can include a programmable processor (not shown) and system components (also not shown) configured to control and/or communicate with the transducer wand 102, the touch-screen display 110, and the I/O port 115. In certain embodiments, the display unit electronics 113 can also carry out other functions, such as storing and accessing data, processing user-input, and communicating over a wireless interface via an internal radio antenna (not shown) or an external radio antenna 116. Because many of the basic structures and functions of processor electronics are known, they have not been shown or described in further detail to avoid unnecessarily obscuring the described embodiments.

Figure 2A:
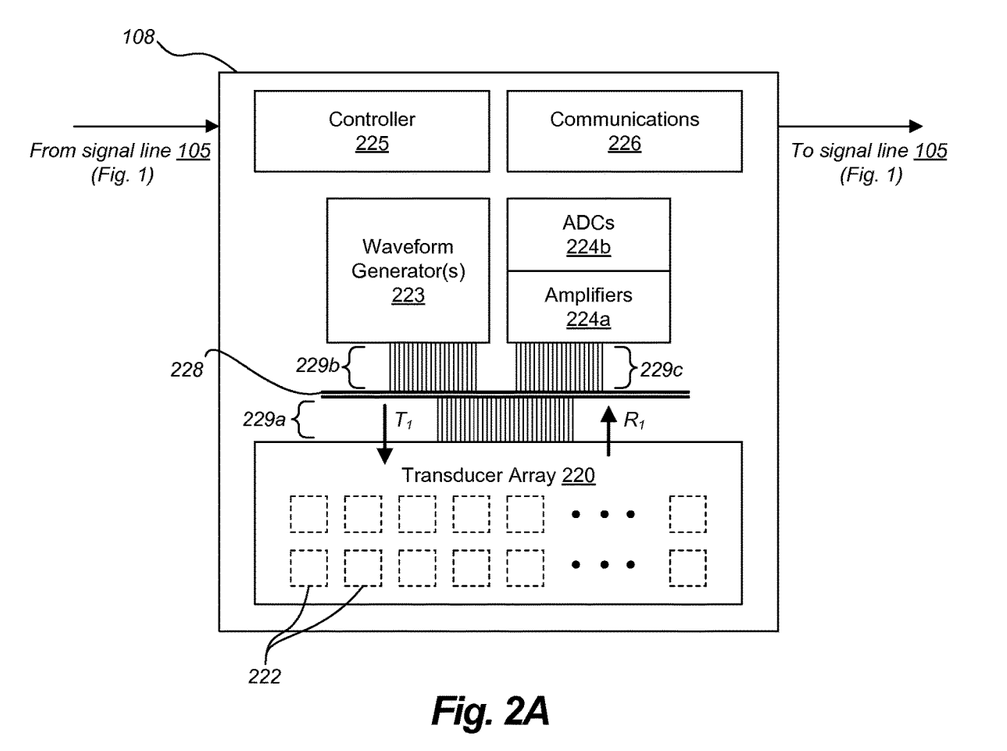
FIG. 2A is a block diagram of transducer electronics of the ultrasound system of FIG. 1 configured in accordance with an embodiment of the present technology.

FIG. 2A is a block diagram of the transducer electronics 108 configured in accordance with an embodiment of the present technology. As shown, the transducer electronics 108 include a transducer array 220 having transducer elements 222 (e.g., 64, 128, or 256 transducer elements; shown schematically), waveform generators 223, amplifiers 224a, and ADCs 224b. In one embodiment, the amplifiers 224a and the ADCs 224b are colocated on the same chip (e.g., application specific integrated circuit (ASIC)) with each other and/or with other circuit components of the transducer electronics 108. In another embodiment, the amplifiers 224a and the ADCs 224b can be formed on separate chips or across multiple chips. As used herein, the term "amplifiers/ADCs" refers to at least one amplifier, at least one ADC, or a combination of at least one amplifier and at least one ADC.

In the illustrated embodiment, the transducer electronics 108 further include a controller 225, communication components 226 (for, e.g., communicating over the signal line 105), a communication bus 228, and channels 229 (shown as a first through third sets of channels 229a-229c). As described in greater detail below, a switch controller (e.g., addressable switches, multiplexers, etc.) can couple individual transducer elements 222 with individual amplifiers 224a and/or individual ADCs 224b. In general, only certain aspects of the transducer electronics 108 are described in detail for purposes of illustration. For example, in various embodiments, the transducer electronics 108 can include a memory for storing processing instructions and data, a clock circuit, a power supply circuit, etc. Other components of the transducer electronics 108 are not described to avoid unnecessarily obscuring the various embodiments of the present technology.

In operation, the transducer electronics 108 communicate with the display unit electronics 113 (FIG. 1) over the signal line 105 and provides "frames" of digital ultrasound information to the display unit electronics 113 to produce and display ultrasound images. The controller 225 gathers these frames by collecting digital data over multiple pulse repetition intervals (PRIs). Over each PRI, the controller uses a transmit signal $T_1$ to control the transducer array 220 (via the waveform generators 223) and a return signal $R_1$ to produce ultrasound information. The transmit signal $T_1$ is based, for example, on forward beam forming and steering signals. The return signal $R_1$ can include acoustic information captured by the transducer array 223 (i.e., captured in response to ultrasonic echos). The controller 225 uses the amplifiers 224a and the ADCs 224b to amplify the return signal $R_1$ and then convert this signal into digital data (e.g., serial data). As digital data is collected for the frame, the controller 225 can carry out additional PRIs (i.e., involving different transmit and receive signals $T_1$ and $R_1$). The controller 225 produces the frames at a certain frame rate (FR) that can be based, for example, on Equation 1:

$$FR=(n \times PRI_{DUR})^{-1} \text{ (Hz)} \quad (1)$$

where $PRI_{DUR}$ is the duration of a PRI. In one embodiment, the FR can be in the range of about 20 to 30 Hz.

As discussed above, amplifiers and ADCs can consume a substantial amount of power. Typically, conventional ultrasound systems collectively enable or disable every amplifier and ADC at the same time, even when not every amplifier and ADC is producing relevant information. For example, only a portion of the amplifiers and ADCs may be needed for suitable beam forming at a given time. As such, conventional systems can waste a substantial amount of power by operating these amplifiers and ADCs when they are not needed. In accordance with various embodiments of the present technology, however, the controller 225 can selectively enable and disable individual amplifiers and ADCs to conserve power. In particular, the controller 225 can disable those amplifiers and ADCs that are not gathering relevant information. At one PRI, the controller 225 can disable individual amplifiers 224a and individual ADCs 224b. At the next PRI, the controller 225 can enable some of the previously disabled amplifiers and ADCs, while disabling other amplifiers and ADCs. In some embodiments, rather than disabling and enabling amplifiers/ADCs over the entire PRI, the controller 225 can enable and disable amplifiers/ADCs over a portion of the PRI. For example, the controller enable 225 can disable amplifiers/ADCs for half of the PRI and then enable those amplifiers/ADCs for the remaining half of the PRI.

Figure 2B:
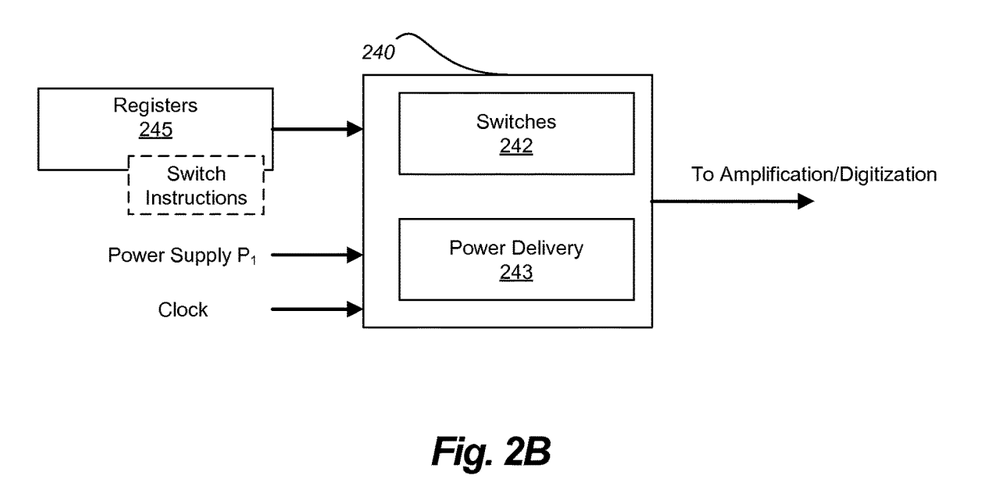
FIG. 2B is a block diagram of a switch controller configured in accordance with an embodiment of the present technology.

FIG. 2B is a block diagram of a switch controller 240 configured in accordance with an embodiment of the present technology. The transducer electronics 108 can incorporate the switch controller 240 at a variety of locations, such as at an amplifier circuit, ADC circuit, and/or another suitable component. The switch controller 240 is operably coupled to individual amplifiers 224a and/or individual ADCs 224b (not shown in FIG. 2B). As shown, the switch controller 240 include switches 242 (e.g., logic gates) and power delivery circuitry 243. In operation, the switch controller 240 is arranged to receive switch instructions that direct the switches 242 to connect a level of power $P_1$ (based, e.g., on a supply voltage) to particular amplifiers 224a and/or particular ADCs 224b. In the illustrated embodiment, the switch instructions are stored at one or more registers 245 that can be loaded, for example, by the controller 225 (FIG. 2A). In one embodiment, the registers 245 are located on the same chip as the amplifiers 224a and/or the ADCs 224b.

In various embodiments, the power delivery circuitry 243 can include capacitors, driver circuits, and other components for delivering an appropriate level of power to the amplifiers 224a and/or ADCs 224b. In one embodiment described in greater detail below, the power delivery circuitry 243 can deliver a minimum level of power to individual amplifiers 224a and/or individual ADCs 224b to maintain a minimum power level to those amplifiers 224a and/or ADCs 224b that are not enabled during a given frame. In an additional or alternate embodiment, the power delivery circuitry 243 can ramp up or ramp down power delivered to individual amplifiers 224a and/or individual ADCs 224b as they are respectively enabled and/or disabled.

Figure 3:
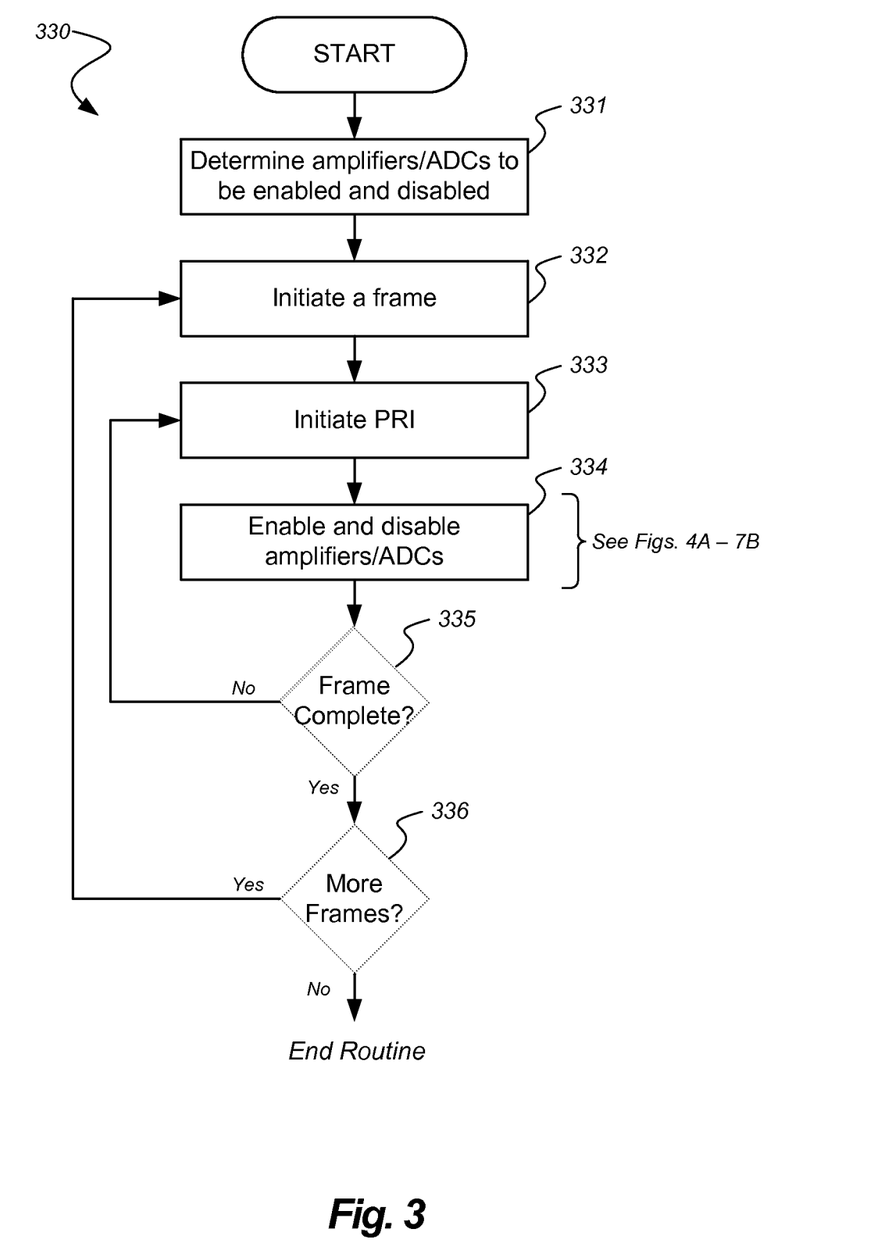
FIG. 3 is a flow diagram illustrating a routine for operating the transducer electronics of FIG. 2A in accordance with an embodiment of the present technology.

FIG. 3 is a flow diagram illustrating a routine 330 for operating the transducer electronics 208 (FIG. 2A) in accordance with an embodiment of the present technology. In one aspect of this embodiment, the routine 330 can be carried out by the controller 225 (FIG. 2A). In other embodiments, however, various aspects of the routine 330 can be carried out without the controller 225. For example, in some embodiments, amplifiers/ADCs can self-regulate power. In these embodiments, the amplifiers/ADCs can include on-chip memory and related logic for carrying out processing instructions, algorithms, etc.

The routine 330 starts when the controller 225 is instructed to begin ultrasound imaging. For example, the routine 330 can begin when a user actuates the input device 109 (FIG. 1) on the transducer wand 102 (FIG. 1). After the start block, the routine proceeds to block 331 to determine which amplifiers/ADCs are to be enabled or disabled over a given PRI. In one embodiment, the routine 330 can make this determination based on instructions from the display unit electronics 113 (FIG. 1). In another embodiment, the routine 330 makes this determination independent of the display unit electronics 113 (based, e.g., on the acquisition geometry). For example, the controller 225 and/or the amplifiers/ADCs themselves can make this determination. In addition, in some embodiments, the routine 330 can dynamically determine which amplifiers/ADCs to enable or disable. For example, the routine 330 can make this determination after completing a PRI, but before completing a frame.

As discussed above, the routine 330 can enable or disable amplifiers/ADCs based on whether particular amplifiers/ADCs are necessary for signal processing, such as whether the particular amplifiers and/or ADCs are necessary for beam forming. In some embodiments, the routine 330 can enable and disable amplifiers/ADCs based on the particular scanning mode or application. The routine 330, for example, can conserve power by operating fewer amplifiers/ADCs in low-resolution, low-depth, or large-aperture (i.e., small F number) scan modes. In another mode, such as in a high-resolution, high-depth, or small-aperture scans, the routine 330 can enable additional amplifiers/ADCs.

In the illustrated embodiment, the routine 330 can determine which amplifiers/ADCs to enable and disable before carrying out a particular frame and/or PRI. For example, the routine can make this determination based on the switching instructions stored at the registers 245. As described in greater detail below, the switching instructions can include logic and/or algorithms for enabling individual amplifiers 224a and/or individual ADCs 224b of the various channels 229 of the transducer electronics 108. Once this determination is made, the routine 330 can proceed to block 332 to begin or initiate a frame. As discussed above, a frame can include digital data acquired over multiple PRIs. The routine 330 can transmit these frames to the display unit electronics 113 (FIG. 1) at various times during the execution of the routine 330 for further processing and eventual display.

After initiating the frame, the routine 330 continues to block 333 to initiate a PRI and then continues to block 334 to enable and disable amplifiers/ADCs. At block 333, the routine 330 can, e.g., connect array elements and amplifiers/ADCs over certain channels, generate a transmit signal, and process a return signal. At block 334, the routine 330 enables and disables amplifiers/ADCs based on its determination at block 331. In one aspect of this embodiment, the routine 330 enables amplifiers/ADCs by connecting power or increasing power and it disables certain amplifiers/ADCs by disconnecting power or reducing power (e.g., via the power delivery circuitry 243; FIG. 2B). In some embodiments, the routine 330 disables amplifiers/ADCs for an entire PRI (described further with reference to FIGS. 4A-4B). In additional or alternate embodiments, the routine 330 disables amplifiers/ADCs over a portion of the PRI (described further with reference to FIGS. 5A-7B).

Once the PRI is complete, the routine 330 proceeds to decision block 335 to determine whether the frame is complete. If the frame is not complete, the routine 330 returns to block 333 to carry out another PRI. If, however, the frame is complete, the routine 330 proceeds to decision block 336 to determine whether to produce additional frames. If more frames are to be produced, the routine 330 proceeds to block 332 to begin another frame; otherwise, the routine 330 can terminate.

Figure 4A:
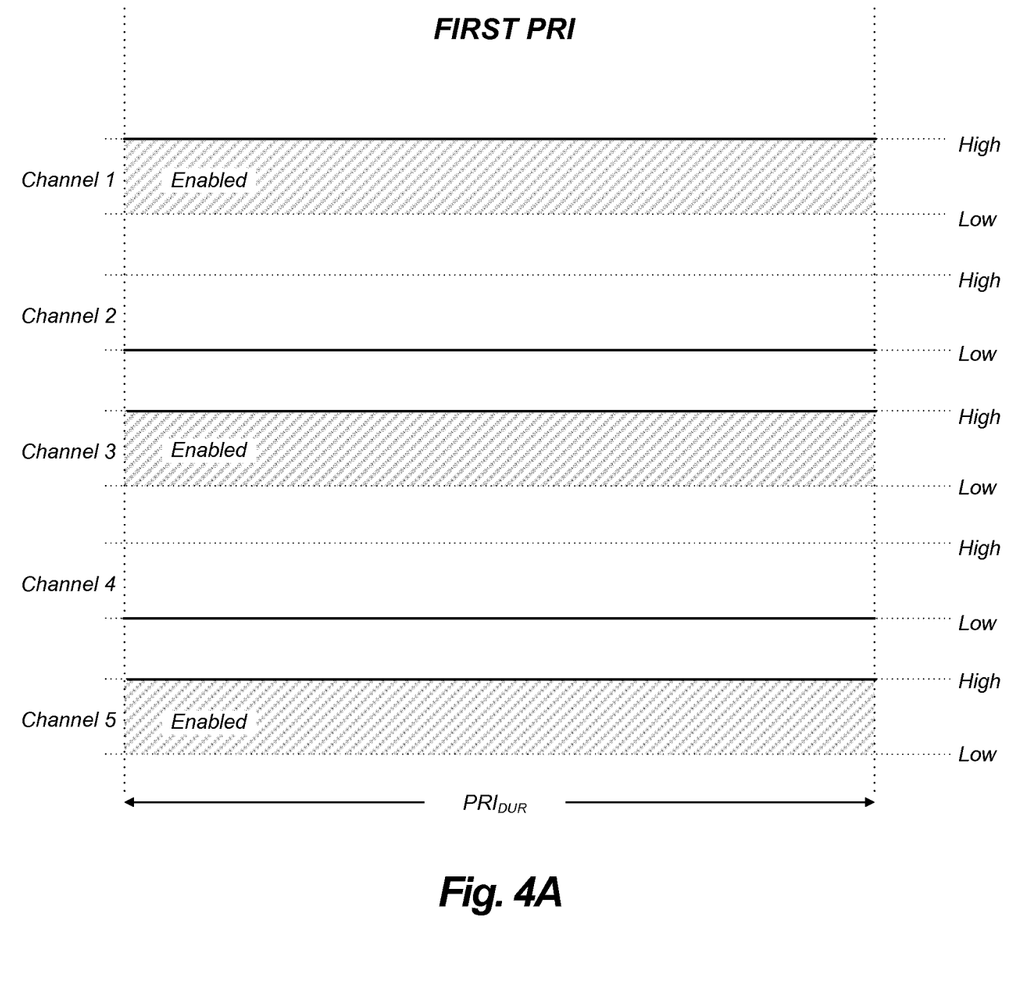
FIGS. 4A and 4B are signal line diagrams representing the power consumed by amplifiers and/or analog to digital converters during execution of the routine of FIG. 3 in accordance with an embodiment of the present technology.
Figure 4B:
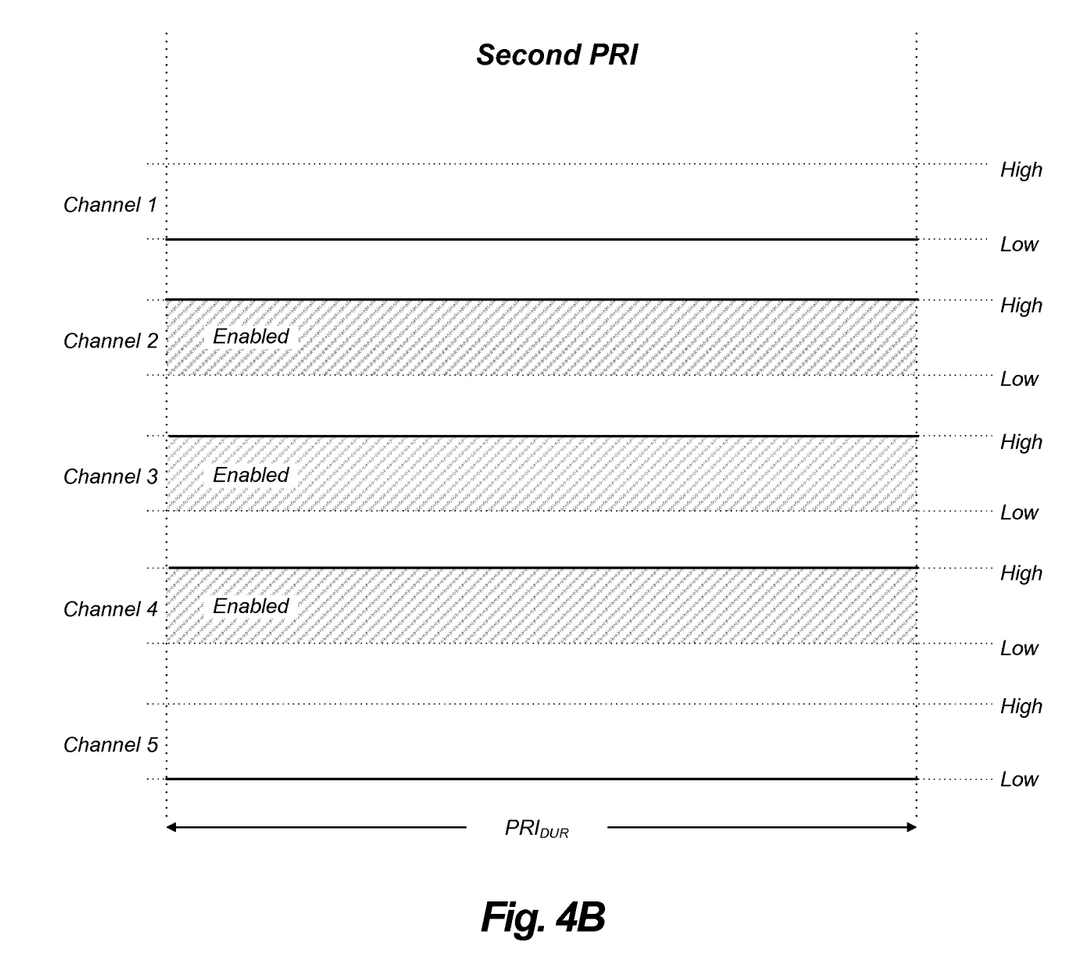

FIGS. 4A and 4B are signal line diagrams representing the power consumed by amplifiers/ADCs over a PRI for certain channels (e.g., the channel 219c in FIG. 2A) in accordance with an embodiment of the present technology. In one embodiment, FIGS. 4A and 4B represent the power consumed while the routine 330 (FIG. 3) is executing blocks 333 and 334 (FIG. 3). The power level "high" generally represents power consumed when amplifiers/ADCs are enabled for a given channel, and the power level "low" generally represents power consumed when amplifiers/ADCs are disabled for a given channel. In the illustrated embodiments, and for purposes of clarity, the signal lines diagrams only show five channels ("channel 1"-"channel 5").

Referring first to FIG. 4A, over a first PRI, the routine 330 enables the amplifiers/ADCs of channels 1, 3, and 5 and disables the amplifiers/ADCs of channels 2 and 4. The routine 330, thus, conserves power that would otherwise be consumed by those amplifier/ADCs not required during the first PRI. In FIG. 4B, over a second PRI occurring after the first PRI, the routine 330 disables the amplifiers/ADCs of channels 1 and 5, enables the amplifiers/ADCs of channels2 and 4, and continues to enable the amplifiers/ADCs of channel 3. Again, the routine 330 conserves power by only powering those amplifiers/ADCs that are needed during the second PRI. After completing the second PRI, the routine 330 can continue to enable and disable amplifiers/ADCs for power conservation over a given PRI.

FIGS. 5A-7B are signal line diagrams representing the power consumed by amplifiers/ADCs over the first and second PRIs (FIGS. 4A and 4B) over various duty cycles of certain channels in accordance with selected embodiments of the present technology.

In the illustrated embodiments, the routine 330 can enable or disable the amplifiers/ADCs for quantized time units $\Delta t_q$. In some embodiments, the time units $\Delta t_q$ can facilitate signal processing. For example, a binary number can represent the duty cycle in increments of the time units $\Delta t_q$. In one aspect of this embodiment, the duration of the PRI can be represented in a number of time units based, for example, on Equation 2:

$$PRI_{DUR} = \sum_{q=0}^{k} \Delta t_q \tag{2}$$

In some embodiments, the duty cycle can account for signal processing delays, such as line overhead delays, transmit delays, etc. For example, as shown in the illustrated embodiments, the various duty cycles account for a line overhead having a duration of 5 $\Delta t_q$. In addition, in certain embodiments, the amplifiers/ADCs can process signals relating to the duty cycle. For example, the amplifiers 224a and/or the ADCs 224b (FIG. 2A) can use the logic to process a binary input or other suitable signal that represents the duty cycle.

Figure 5A:
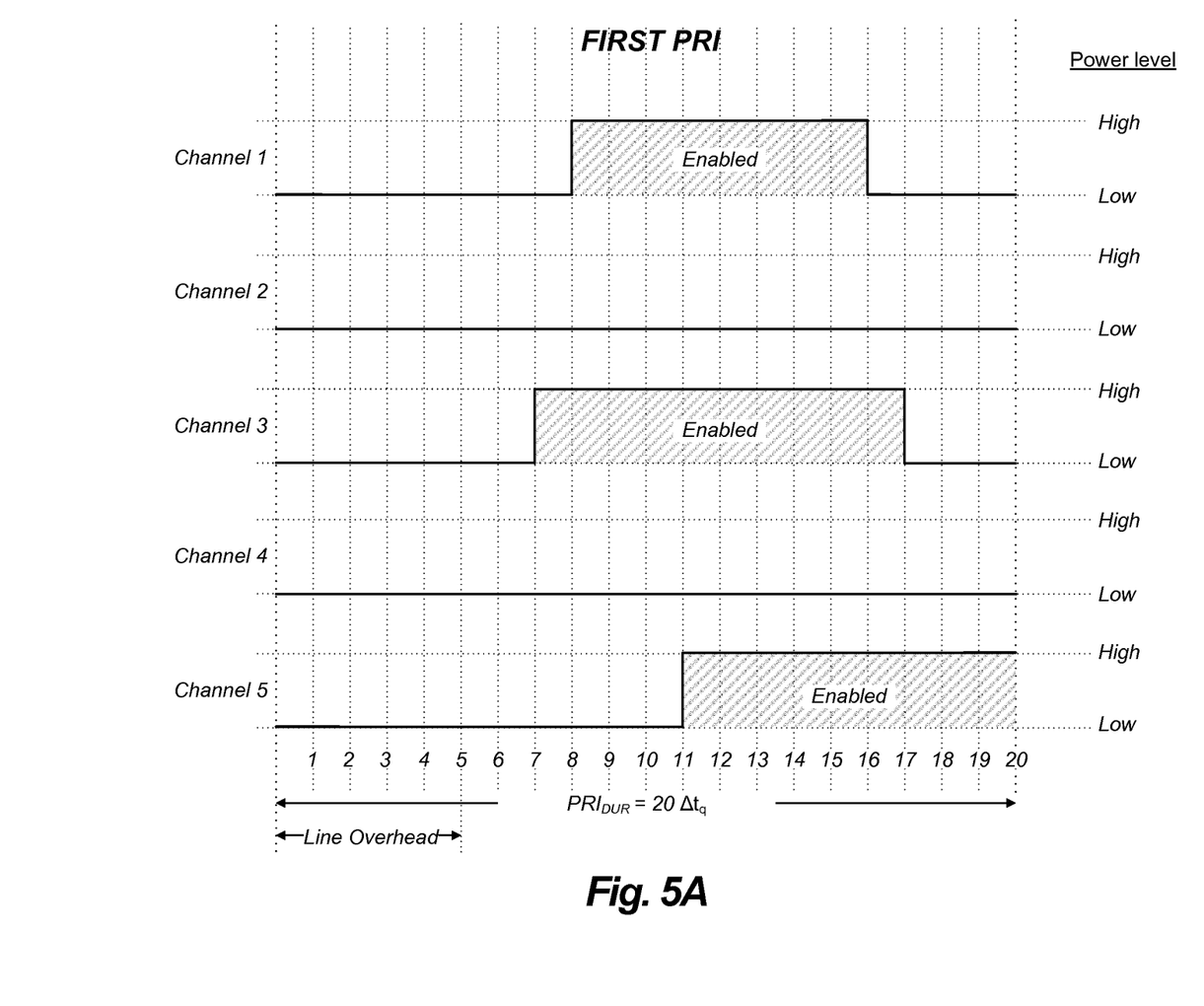
Figure 5B:
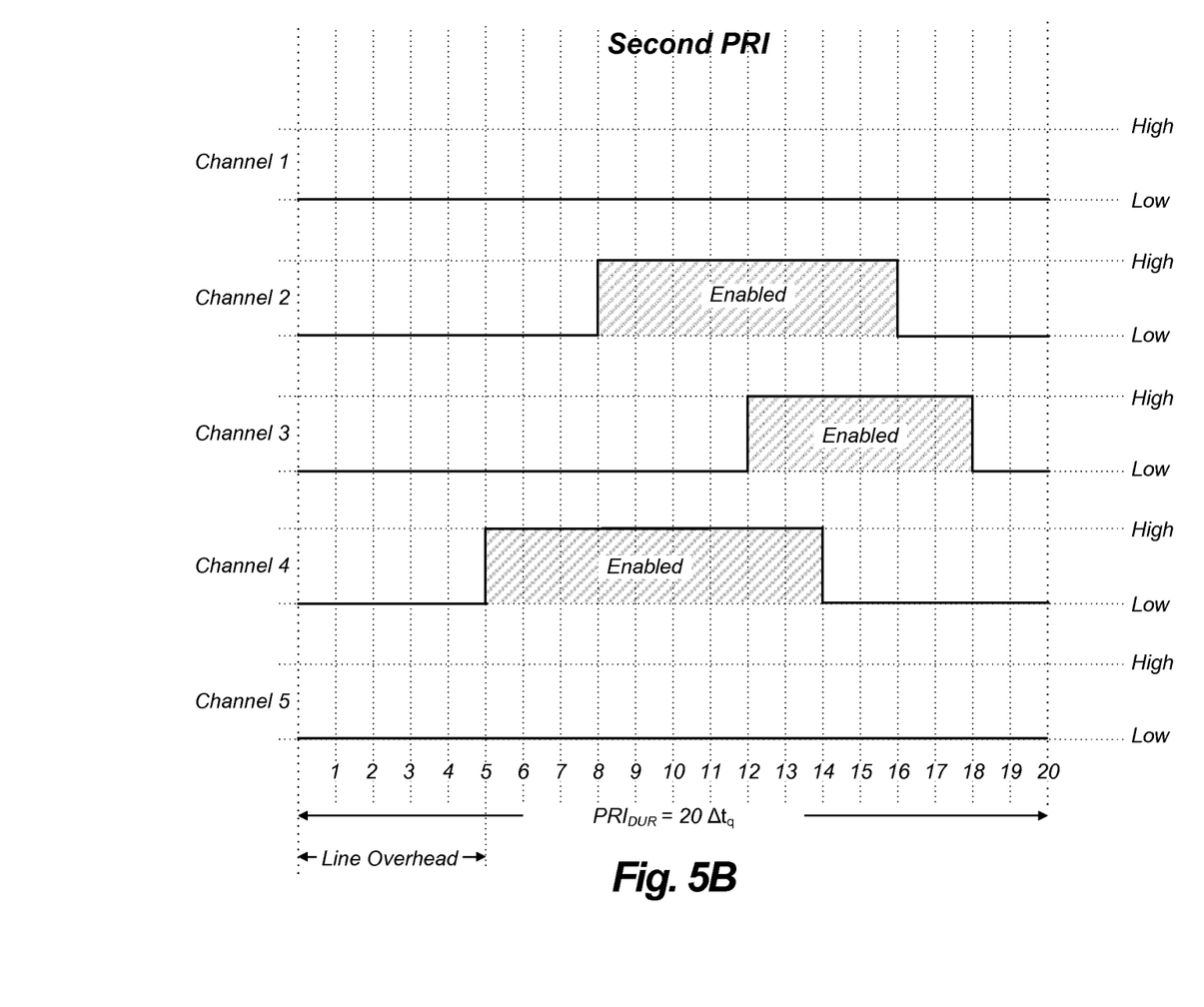

Referring to FIGS. 5A-5B, the routine 330 enables and disables the amplifiers/ADCs of channels 1-5 according to different duty cycles. Over the first PRI (FIG. 5A), the routine 330 disables channels 2 and 4 for the duration of the first PRI. Over channels 1, 3, and 5, however, the routine 330 enables and disables the amplifiers/ADCs according to a different duty cycles. In particular, at channel 1, the routine 330 enables amplifiers/ADCs after 8 $\Delta t_q$ have elapsed and then disables the amplifiers/ADC after 16 $\Delta t_q$ have elapsed. At channel 3, the routine 330 enables the amplifiers/ADCs after 7 $\Delta t_q$ have elapsed and then disables the amplifiers/ADCs after 17 $\Delta t_q$ have elapsed. At channel 5, the routine

330 enables the amplifiers/ADCs after 11 $\Delta t_q$ have elapsed and does not disable the amplifiers/ADCs for the remainder of the first PRI.

Over the second PRI (FIG. 5B), the routine 330 disables channels 1 and 5 for the duration of the second PRI. Over channels 2, 3, and 5, however, the routine 330 enables the amplifiers/ADCs at different increments of the time units $\Delta t_q$ (at 8 $\Delta t_q$ for channel 2, at 12 $\Delta t_q$ for channel 3, and at 5 $\Delta t_q$ for channel 4). After they have been enabled for a certain number of increments, the routine 330 disables the amplifiers/ADCs of the channels 2, 3, 5 (at 16 $\Delta t_q$ for channel 2, at 8 $\Delta t_q$ for channel 3, and at 14 $\Delta t_q$ for channel 4).

Figure 6A:
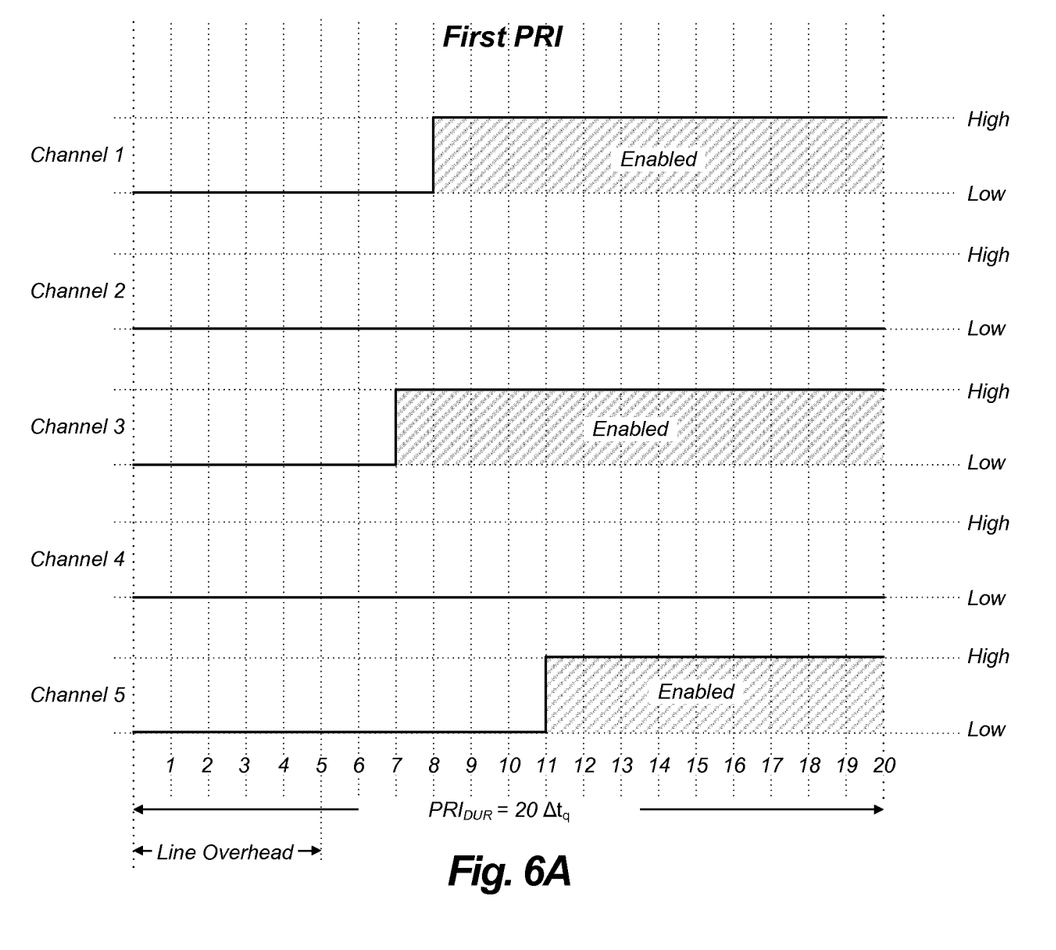
Figure 6B:
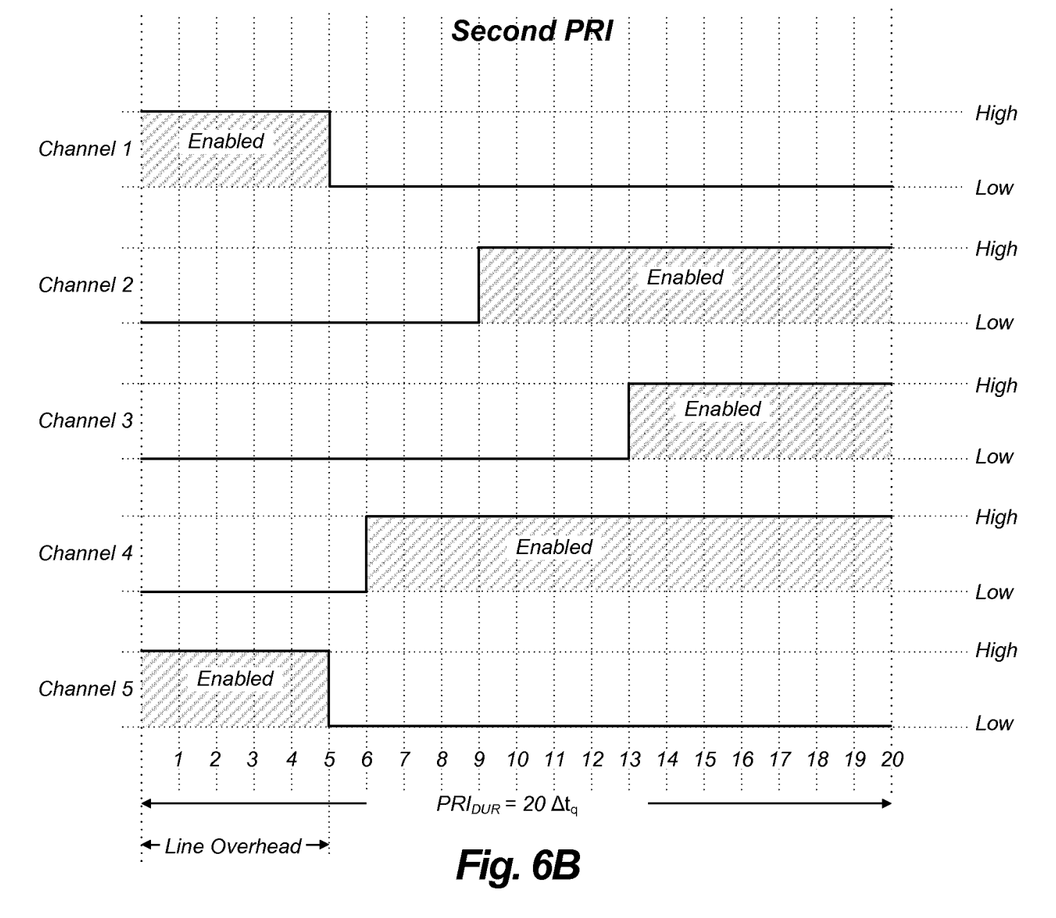

Referring to FIGS. 6A-6B, and similar to FIGS. 5A-5B, the routine 330 enables and disables the amplifiers/ADCs of channels 1-5 according to different duty cycles. However, the routine 330 only changes the state of the amplifiers/ADCs a single time over a PRI (i.e., from enabled to disabled or from disabled to enabled). Over the first PRI (FIG. 6A), the routine 330 enables and disables the same amplifiers/ADCs as shown in FIG. 5A. However, the routine 330 does not disable the channels 1, 3, 5 after they have been enabled. Similarly, over the second PRI (FIG. 6B), the routine 330 enables and disables the same amplifiers/ADCs as shown in FIG. 5B, but does not disable channels 2, 3, and 4 after they have been enabled. FIG. 6B also shows the routine 330 accounting for the line overhead in the duty cycle. In particular, the routine 330 does not disable the channels 1 and 5 until 5 $\Delta t_q$ have elapsed.

Figure 7A:
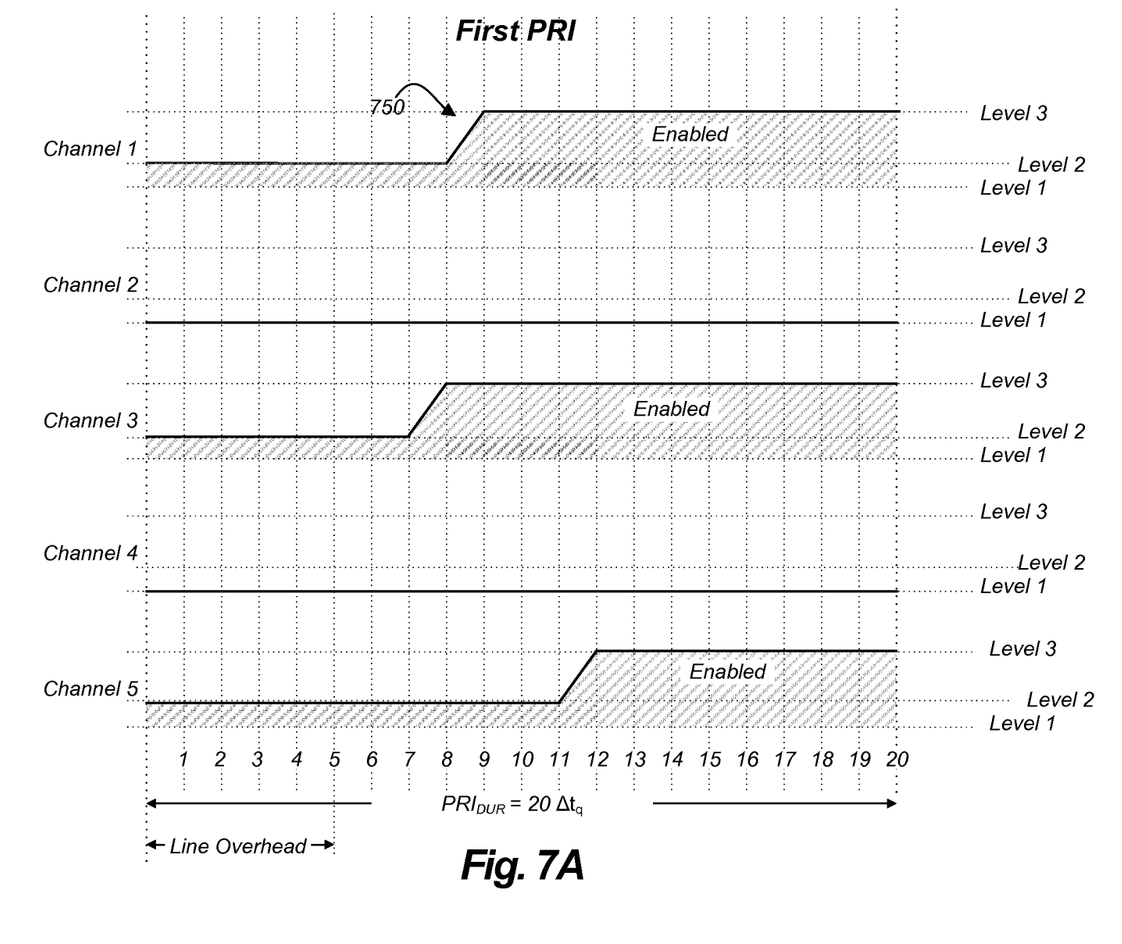
Figure 7B:
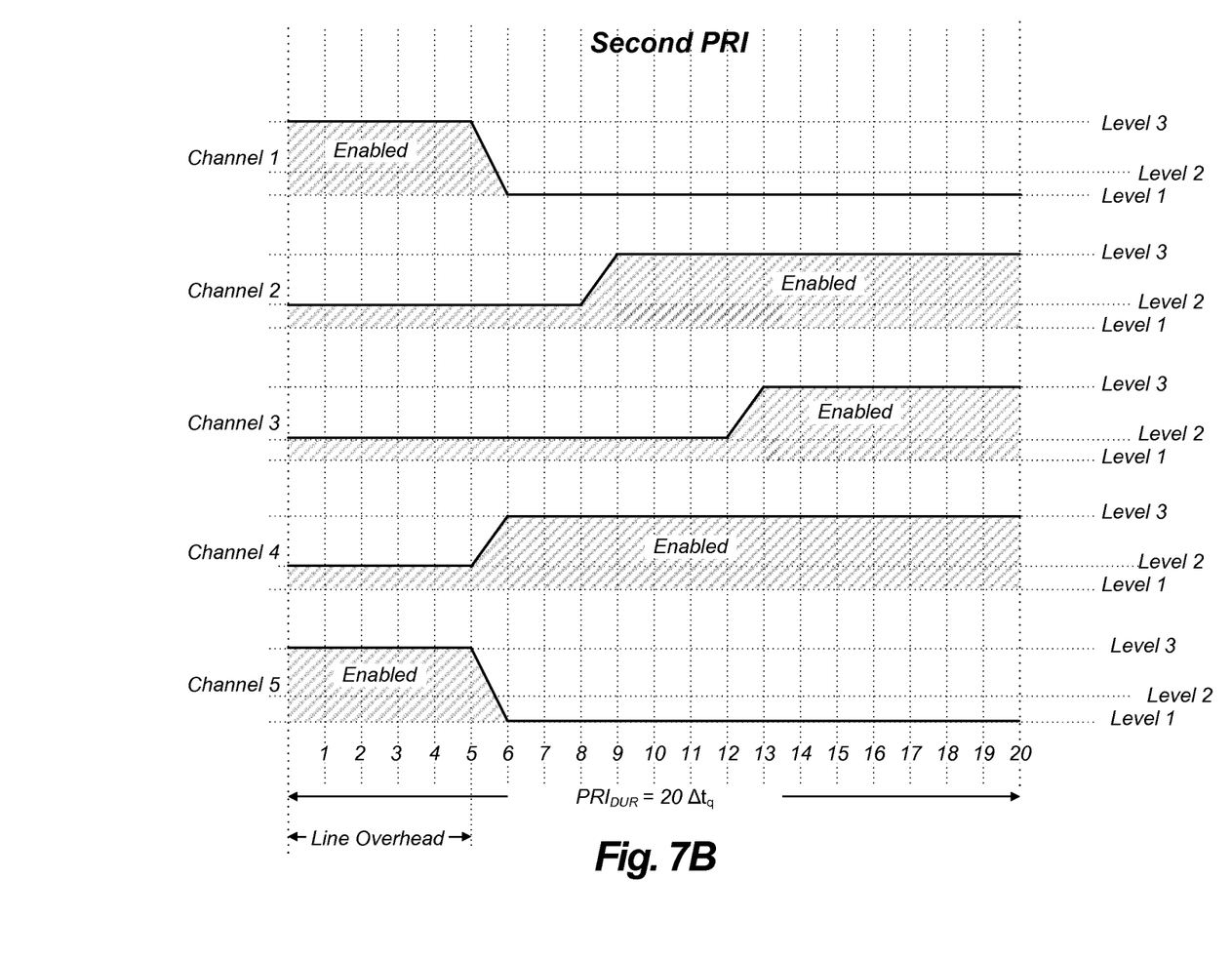

Referring to FIGS. 7A-7B, and similar to FIGS. 6A-6B, the routine 330 enables and disables the amplifiers/ADCs of channels 1-5 according to different duty cycles. However, the amplifiers/ADCs operate at different power levels. Over the first PRI (FIG. 7A), the routine 330 enables and disables the same amplifiers/ADCs as shown in FIG. 6A, but maintains the amplifier/ADCs of channels 1, 3, and 5 at a second power level (e.g., a standby power level) before enabling them. For those channels not being enabled (i.e., channels 2 and 4), the routine 330, maintains the amplifiers/ADCs at a first power level (e.g., zero power level). In some embodiments, the routine 330 can use multiple power levels to facilitate switching speed. For example, the routine 330 can hold the amplifiers/ADCs at the second power level to charge capacitors and/or initialize other components to reduce signal delay. On the other hand, the routine 330 can hold the other (disabled) amplifiers/ADCs at the first power level to conserve additional power. In certain embodiments, the routine 330 can also account for ramp-up times (shown as a ramp 750 in the signal lines) in the duty cycle. Similarly, over the second PRI (FIG. 7B), the routine 330 can enable and disables the amplifiers/ADCs over the second PRI, but with more than two power levels. In certain embodiments, the power delivery circuitry 243 (FIG. 2B) can be configured to deliver multiple power levels.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

From the foregoing, it will be appreciated that specific embodiments of the disclosure have been described herein for purposes of illustration, but that various modifications may be made without deviating from the disclosure. For example, the various waveforms shown in the Figures can have different slopes, magnitudes, shapes, etc. In addition, certain aspects of the disclosure described in the context of particular embodiments may be combined or eliminated in other embodiments. Further, while advantages associated with certain embodiments have been described in the context of those embodiments, other embodiments may also exhibit such advantages. Not all embodiments need necessarily exhibit such advantages to fall within the scope of the present disclosure. Accordingly, the disclosure and associated technology can encompass other embodiments not expressly shown or described herein.

I claim:

1. A method for conserving power in a portable ultrasound system having transducer electronics that include a plurality of transducer elements, a plurality of amplifiers, a plurality of analog to digital converters (ADCs), and a switch controller configured to couple individual transducer elements with individual amplifiers and individual ADCs, the method comprising:

initiating a first pulse repetition interval (PRI), disabling at least one first ADC of the plurality of ADCs via the switch controller, wherein the disabling includes removing or reducing power from the first ADC, and initiating a second PRI comprising a plurality of time units, enabling, during the second PRI, the first ADC at a first portion of the plurality of time units and at least one other ADC of the plurality of ADCs at a second portion of the plurality of time units via the switch controller, wherein the enabling includes supplying or increasing power to the first ADC at the first portion of the plurality of time units according to a first duty cycle and supplying or increasing power to the at least one other ADC at the second portion of the plurality of time units according to a second duty cycle, wherein the second portion and the first portion are different portions, and disabling at least one second ADC of the plurality of ADCs via the switch controller.

2. The method of claim 1 wherein:
disabling the first ADC comprises removing power from the first ADC; and
enabling the first ADC comprises supplying power to the first ADC.

3. The method of claim 1, further comprising disabling at least one first amplifier of the plurality of amplifiers upon initiation of the first PRI, and
enabling the first amplifier upon initiation of the second PRI, wherein disabling the at least one first amplifier comprises removing or reducing power from the at least one first amplifier over the entire duration of the first PRI while other amplifiers of the plurality of amplifiers are enabled.

4. The method of claim 1, further comprising disabling at least one first amplifier of the plurality of amplifiers upon initiation of the first PRI, by removing or reducing power from the first amplifier over a portion of the duration of the first PRI while other amplifiers of the plurality of amplifiers are enabled.

5. The method of claim 4 wherein the portion of the duration is based on a duty cycle in which the first amplifier is alternatingly enabled and disabled over the first PRI.

6. The method of claim 5 wherein:
the portion of the duration of the first PRI is based on a plurality of predetermined,
quantized time units; and the duty cycle has a pulse width that starts after a first number of time units within the first PRI and stops after a second number of time units within the first PRI.

7. The method of claim 1 wherein the transducer electronics include a plurality of channels having at least a first channel associated with the first ADC, and at least a second channel associated with the second ADC.

8. The method of claim 1 wherein the at least one second ADC is disabled according to a third duty cycle.

9. The method of claim 8 further comprising upon initiation of the second PRI, disabling at least one third ADC of the plurality of ADCs according to a fourth duty cycle, wherein the fourth and third duty cycles have different start times, but the same stop time.

10. The method of claim 1 wherein: disabling the first ADC includes maintaining the first ADC at a first power level; and
enabling the first ADC includes maintaining the first ADC at a second power level greater than the first power level.

11. The method of claim 10 wherein the first power level is a standby power level.

12. The method of claim 10 wherein the first power level is a zero power level.

13. A portable ultrasound system, comprising:
a plurality of transducer elements;
a plurality of analog to digital converters (ADCs), including a first ADC and a second ADC, and
a switch controller operably coupled to the plurality of transducer elements and the plurality of ADCs, wherein the switch controller is configured to operably couple individual transducer elements with the first ADC and second ADC,
remove or reduce power from the first ADC upon initiation of a first pulse repetition interval (PRI), and
upon initiation of a second PRI comprising a plurality of time units, supply or increase power to the first ADC at a first portion of the plurality of time units according to a first duty cycle and supply or increase power to at least one other ADC of the plurality of ADCs at a second portion of the plurality of time units according to a second duty cycle and disable the second ADC, wherein the second portion and the first portion are different portions.

14. The portable ultrasound system of claim 13, further comprising a plurality of amplifiers, wherein the plurality of amplifiers includes a first amplifier and a second amplifier, and wherein the switch controller is further configured to:
operably couple the individual transducer elements with the first and second amplifiers; connect power to the second amplifier and disconnect power from the first amplifier upon the initiation of the first PRI; and
connect power to the first amplifier and disconnect power from the second amplifier upon the initiation of the second PRI.

15. The portable ultrasound system of claim 13 wherein the switch controller is further configured to:
maintain the first ADC at a first power level upon initiation of the first PM; and
maintain the first ADC at a second power level greater than the first power level upon initiation of the second PRI.

16. The portable ultrasound system of claim 15 wherein the first power level is a standby power level.

17. The portable ultrasound system of claim 15 wherein the first power level is a zero power level.

18. A portable ultrasound apparatus, comprising:
a processor;
a plurality of transducer elements coupled to the processor;
a plurality of analog to digital converters (ADCs) coupled to the processor;
a plurality of amplifiers coupled to the processor;
wherein the processor is configured to selectively enable fewer than all of the ADCs and amplifiers during a first pulse repetition interval (PRI) comprising a plurality of time units so that at least a first ADC of the plurality of ADC and a first amplifier of the plurality of amplifiers are enabled at a first portion of the plurality of time units during the first PRI according to a first duty cycle and at least one other ADC of the plurality of ADCs is enabled at a second portion of the plurality of time units during the first PRI according to a second duty cycle, wherein the second portion and the first portion are different portions, and at least a second ADC of the plurality of ADC and a second amplifier of the plurality of amplifiers are disabled during the first PRI, and
wherein the processor is configured to selectively enable fewer than all of the ADCs and amplifiers during a second PRI so that at least the first ADC and the first amplifier are disabled during the second PRI, and at least the second ADC and the second amplifier are enabled during the second PRI.

* * * * *